(12) United States Patent
Chen et al.

(10) Patent No.: US 12,122,696 B2
(45) Date of Patent: Oct. 22, 2024

(54) METHOD OF REDUCING AND CONTROLLING HAZARDOUS SUBSTANCE IN PROCESS OF HIGH-VALUE BIOLOGICAL CONVERSION OF URBAN ORGANIC WASTE

(71) Applicants: Tongji University, Shanghai (CN); Shanghai Municipal Engineering Design Institute (Group) Co., Ltd., Shanghai (CN)

(72) Inventors: Yinguang Chen, Shanghai (CN); Xiong Zheng, Shanghai (CN); Leiyu Feng, Shanghai (CN); Haining Huang, Shanghai (CN); Jianying Xiong, Shanghai (CN); Xin Zhang, Shanghai (CN); Lei Dong, Shanghai (CN)

(73) Assignees: Tongji University, Shanghai (CN); Shanghai Municipal Engineering Design Institute (Group) Co., Ltd., Shanghai (CN)

( * ) Notice: Subject to any disclaimer, the term of this patent is extended or adjusted under 35 U.S.C. 154(b) by 65 days.

(21) Appl. No.: 17/561,860

(22) Filed: Dec. 24, 2021

(65) Prior Publication Data
US 2022/0234932 A1    Jul. 28, 2022

(30) Foreign Application Priority Data
Jan. 22, 2021    (CN) .......................... 202110086988.8

(51) Int. Cl.
C02F 11/04    (2006.01)
B09B 3/65    (2022.01)
(Continued)

(52) U.S. Cl.
CPC ................. *C02F 11/04* (2013.01); *B09B 3/65* (2022.01); *C02F 1/66* (2013.01); *C02F 11/004* (2013.01);
(Continued)

(58) Field of Classification Search
CPC .......... C02F 11/04; C02F 11/147; C02F 1/66; C02F 11/004; C02F 11/02; C02F 3/341;
(Continued)

(56) References Cited

U.S. PATENT DOCUMENTS 5,616,241 A * 4/1997 Khudenko ............ C02F 3/2806
                                                    210/151
8,372,283 B2 * 2/2013 Theodore .................. C02F 1/66
                                                    210/605
(Continued)

FOREIGN PATENT DOCUMENTS

CN    101913747 A    * 12/2010
CN    102718318 A    * 10/2012
(Continued)

OTHER PUBLICATIONS

Machine-generated English translation of KR 101757210, generated on Jun. 26, 2023.*
(Continued)

*Primary Examiner* — Fred Prince
(74) *Attorney, Agent, or Firm* — Locke Lord LLP; Tim Tingkang Xia, Esq.

(57) ABSTRACT

The present invention provides a method of reducing and controlling a hazardous substance in a process of high-value biological conversion of an urban organic waste. The method includes: 1) mixing a sludge, a first urban organic waste and an organic acid with water for acclimation to obtain an acclimatized sludge; 2) stage 1 of biological conversion: mixing the acclimatized sludge with a second
(Continued)

urban organic waste to perform anaerobic culture; 3) stage 2 of biological conversion: adding nitrate and bacteria to continue anaerobic culture so as to obtain an organic acid. In the present invention, sludge microbes are acclimatized and then added to high-value chemicals such as acetic acid, propanoic acid and lactic acid prepared in biological conversion of the urban organic waste and then added with bacteria. Thus, by controlling pH value, microbe addition amount and nitrate concentration, the unfavorable effect of the antibiotics and heavy metal ions.

10 Claims, 1 Drawing Sheet

(51) Int. Cl.
| | |
|---|---|
| C02F 1/66 | (2023.01) |
| C02F 3/34 | (2023.01) |
| C02F 11/00 | (2006.01) |
| C02F 11/02 | (2006.01) |
| C02F 11/14 | (2019.01) |
| C02F 11/147 | (2019.01) |
| C12P 7/52 | (2006.01) |
| C12P 7/54 | (2006.01) |
| C12P 7/56 | (2006.01) |
| C12P 39/00 | (2006.01) |
| B09B 101/70 | (2022.01) |
| C02F 101/10 | (2006.01) |
| C02F 101/20 | (2006.01) |
| C02F 101/22 | (2006.01) |
| C02F 101/34 | (2006.01) |
| C02F 101/38 | (2006.01) |
| C02F 103/34 | (2006.01) |

(52) U.S. Cl.
CPC ............ *C02F 11/02* (2013.01); *C02F 11/147* (2019.01); *C12P 7/52* (2013.01); *C12P 7/54* (2013.01); *C12P 7/56* (2013.01); *C12P 39/00* (2013.01); *B09B 2101/70* (2022.01); *C02F 3/341* (2013.01); *C02F 2101/103* (2013.01); *C02F 2101/20* (2013.01); *C02F 2101/22* (2013.01); *C02F 2101/34* (2013.01); *C02F 2101/38* (2013.01); *C02F 2101/40* (2013.01); *C02F 2103/343* (2013.01)

(58) Field of Classification Search
CPC ............ C02F 2101/103; C02F 2101/20; C02F 2101/22; C02F 2101/34; C02F 2101/38; C02F 2101/40; C02F 2103/343; B09B 3/65; B09B 2101/70; C12P 7/52; C12P 7/54; C12P 7/56; C12P 39/00
USPC .............. 210/631, 912, 913, 914, 903, 908; 435/262, 262.5
See application file for complete search history.

(56) References Cited

U.S. PATENT DOCUMENTS

| | | | |
|---|---|---|---|
| 8,900,840 B2 * | 12/2014 | Hafez .................... | C12M 29/26 435/167 |
| 2005/0145566 A1 * | 7/2005 | Haase .................... | C02F 11/148 210/620 |
| 2014/0034574 A1 * | 2/2014 | Josse ..................... | C02F 11/121 210/601 |
| 2015/0191754 A1 * | 7/2015 | Chen ........................ | C12P 7/40 435/141 |
| 2018/0370867 A1 * | 12/2018 | Lu ............................ | A01G 24/60 |
| 2019/0039932 A1 * | 2/2019 | Flannery .................. | C02F 1/58 |
| 2019/0119138 A1 * | 4/2019 | Maher .................. | C02F 11/127 |

FOREIGN PATENT DOCUMENTS

| | | | |
|---|---|---|---|
| CN | 112142281 A | * | 12/2020 |
| DE | 102019112513 A1 | * | 11/2020 |
| EP | 3502230 A1 | * | 6/2019 |
| KR | 20030087673 A | * | 11/2003 |
| KR | 101757210 B1 | * | 7/2017 |
| WO | WO 2020/056335 A1 | * | 3/2020 |

OTHER PUBLICATIONS

Machine-generated English translation of KR 20030087673, generated on Jun. 26, 2023.*
Machine-generated English translation of CN 101913747, generated on Nov. 16, 2023.*
Machine-generated English translation of CN 102718318, generated on Nov. 16, 2023.*
Machine-generated English translation of DE 102019112513, generated on Nov. 16, 2023.*
Machine-generated English translation of CN 112142281, generated on Nov. 16, 2023.*
Di Cesare et al., Co-occurrence of integrase 1, antibiotic and heavy metal resistance genes in municipal wastewater treatment plants, (2016), Water Research, vol. 94, pp. 208-214.*

\* cited by examiner

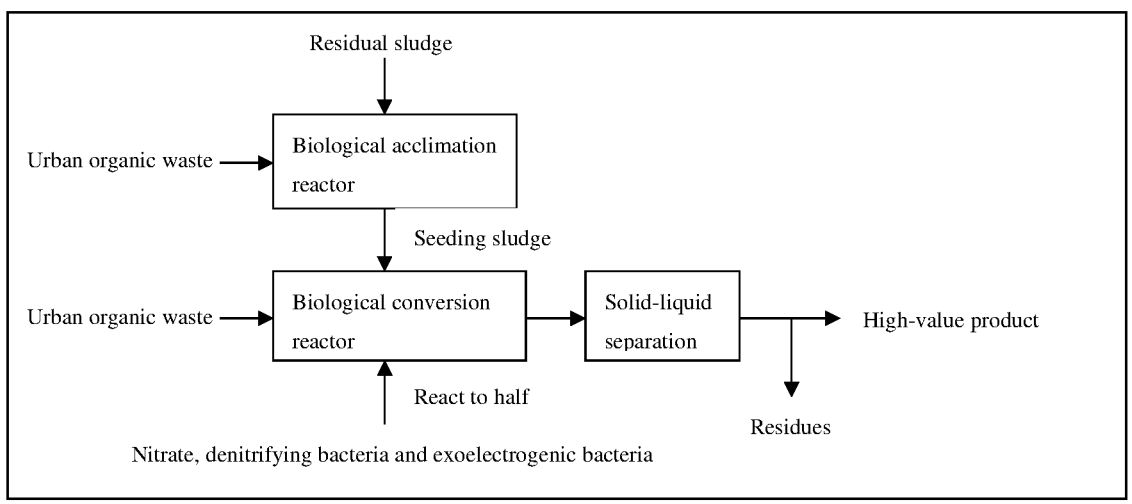

METHOD OF REDUCING AND CONTROLLING HAZARDOUS SUBSTANCE IN PROCESS OF HIGH-VALUE BIOLOGICAL CONVERSION OF URBAN ORGANIC WASTE

CROSS-REFERENCE TO RELATED APPLICATION

This application claims priority from, Chinese patent application number 2021100869888, filed Jan. 22, 2021, the content of which is incorporated herein in the entirety by reference.

TECHNICAL FIELD

The present invention relates to the field of urban organic waste treatments, and in particular to a method of reducing and controlling a hazardous substance in a process of high-value biological conversion of an urban organic waste.

BACKGROUND

With rapid development or Chinese urbanization, the amount of the urban organic waste generated (including restaurant garbage and kitchen garbage and the like) is sharply increasing. Urban organic waste contains a large amount of carbohydrates, protein substances and the like, and are directly discharged into the environment without treatment, leading to severe environmental pollution and waste of organic resources. One method to improve a utilization value of the organic waste is to convert the organic waste into energy source substances such as methane and hydrogen by a biological method. In contrast with the conventional method of converting the urban organic waste into methane and hydrogen, a biological method is employed to convert the urban organic waste into liquid chemicals such as acetic acid, propanoic acid and lactic acid in an open system. This method has the advantages of simple operation, easy transportation and storage of products and low requirements for surrounding safety levels. Therefore, in recent years, it has become a topic of increased interest at home and abroad.

Detection frequency of antibiotics and heavy metal ions in urban organic waste is also increasing. In addition to causing chemical environmental pollution, antibiotics may also induce microbes in the environment to mutate and produce resistance genes and may harm human health when spread. The discharge of excess heavy metal ions into environments will not only pose severe harm to systems including bodies of water, aquatic plants, and aquatic animals, but may also affect human health through the food chain, bringing about diseases such as gout-like syndromes, arthralgia and kidney injury. Furthermore, in a system of high-value biological conversion of urban organic waste, the presence of excess antibiotics and heavy metal ions may also produce noticeable inhibition effects on the activity of microbes. Therefore, research and development of a method of reducing and eliminating an unfavorable effect of antibiotics and heavy metal on a high-value biological conversion of urban organic waste may be significant for improving the effect of high-value biological conversion of urban organic waste and reducing the unfavorable effect of antibiotics and heavy metal in the organic waste residues on the environment.

At present, antibiotics are mainly treated by methods such as the artificial wetland method, soil infiltration method, ultrasonic degradation method and low-temperature plasma method. The heavy metal ions are mainly removed by methods such as the chemical precipitation method, oxidation reduction treatment, solvent extraction separation, adsorption method, membrane separation method and ion exchange method. If a new method of reducing and eliminating an unfavorable effect of antibiotics and heavy metal on high-value biological conversion of urban organic waste can be developed based on consideration of an inhibition effect of the antibiotics and heavy metal ions on the high-value biological conversion of urban organic waste, there may be improvement in high-value utilization levels of urban organic waste and product quality and reduction in secondary pollution to the environment resulting from release of hazardous substances in solid or liquid residues.

SUMMARY

In order to solve the above defects of the prior art, the present invention provides a method of reducing and controlling a hazardous substance in a process of high-value biological conversion of an urban organic waste so as to solve the difficulties in the prior art.

In order to achieve the above object and other relevant objects, the present invention is achieved in the following technical solution.

One of the objects of the present invention is to provide a method of reducing and controlling a hazardous substance in a process of high-value biological conversion of an urban organic waste. The method includes the following steps:

1) acclimation stage: mixing a sludge, a first urban organic waste and an organic acid with water for acclimation to obtain an acclimatized sludge;
2) stage 1 of biological conversion: mixing the acclimatized sludge with a second urban organic waste to perform anaerobic culture;
3) stage 2 of biological conversion: adding nitrate and bacteria to continue anaerobic culture so as to obtain an organic acid;

Preferably, the sludge is a residual sludge of a wastewater treatment plant, a pH of the sludge is 6.0-7.0, a suspended solid concentration is 900 mg/L-10400 mg/L, and a molar ratio of carbon to nitrogen is 5.0-7.5; the main properties of the first urban organic waste and the second urban organic waste are as follows: a pH is 5.0-6.5, a suspended solid concentration is 8000 mg/L-81600 mg/L, and a molar ratio of carbon to nitrogen is 18-27. In the present invention, suspended solid is measured with reference to stipulations of Monitoring Analysis method of Water and Wastewater (fourth version) (China Environmental Science Press House, December 2002).

Preferably, in step 1), a dry weight ratio of the sludge to the first urban organic waste is 1:(7-11).

More preferably, the dry weight ratio of the sludge to the first urban organic waste is 1:(8-10).

Preferably, in step 1), the acclimation condition is that a pH value is 4-11 and an acclimation temperature is 5° C.-80° C.

Preferably, in step 1), the acid is acetic acid, propanoic acid or lactic acid.

Preferably, in step 1), a content of a solid in the mixture formed by mixing is 2000 mg/L-10000 mg/L. In the present invention, the content of the solid is measured with reference to stipulations of Monitoring Analysis method of Water and Wastewater (fourth version) (China Environmental Science Press House, December 2002).

Preferably, in step 1), a concentration of an acid in the mixture formed by mixing is 50 mg/L-3000 mg/L.

More preferably, when the acid is acetic acid, an acclimation condition is that: a pH value is 8-10, and a temperature is 24° C.-26° C.; a concentration of acetic acid is 2000~2200 mg/L.

Further preferably, when the acid is acetic acid, the acclimation condition is that: the pH value is 9, and the temperature is 25° C.; the concentration of acetic acid is 2100 mg/L.

More preferably, when the acid is propanoic acid, an acclimation condition is that: a pH value is 8-10, and a temperature is 24° C.-26° C.; a concentration of propanoic acid is 1100-1300 mg/L.

Further preferably, when the acid is propanoic acid, the acclimation condition is that the pH value is 8 and the temperature is 25° C.; the concentration of propanoic acid is 1200 mg/L.

More preferably, when the acid is lactic acid, an acclimation condition is that a pH value is 5.5-7.5, and a temperature is 24° C.-26° C.; a concentration of lactic acid is 500-700 mg/L.

More preferably, when the acid is lactic acid, the acclimation condition is that the pH value is 6.5, and the temperature is 25° C.; the concentration of lactic acid is 600 mg/L.

Preferably, in step 2), a dry weight ratio of the acclimatized sludge to the second urban organic waste is (0.5-30):100.

More preferably, the dry weight ratio of the acclimatized sludge to the second urban organic waste is (6-10):100.

Preferably, in step 2), the mixture formed by mixing further includes water, and a concentration of a solid in the mixture is 5000 mg/L-70000 mg/L.

More preferably, the concentration of the solid in the mixture is 5500 mg/L-30000 mg/L.

Preferably, in step 2), a condition of the anaerobic culture is that: a pH value is 4-11, a time is 0.5 d-6 d, and a temperature is 5° C.-80° C.

More preferably, when the acid is acetic acid, the condition of the anaerobic culture is that the pH value is 8-10, the time is 5 d-6 d, and the temperature is 24° C.-26° C.

More preferably, when the acid is acetic acid, the condition of the anaerobic culture is that the pH value is 9, the time is 6 d, and the temperature is 25° C.

More preferably, when the acid is propanoic acid, the condition of the anaerobic culture is that the pH value is 7-9, the time is 4 d-6 d, and the temperature is 24° C.-26° C.

Further preferably, when the acid is acetic acid, the condition of the anaerobic culture is that the pH value is 8, the time is 5 d, and the temperature is 25° C.

More preferably, when the acid is lactic acid, the condition of the anaerobic culture is that the pH value is 5.5-7.5, the time is 3 d-5 d, and the temperature is 24° C.-26° C.

Further preferably, when the acid is acetic acid, the condition of the anaerobic culture is that the pH value is 6.5, the time is 4 d, and the temperature is 25° C.

Preferably, in step 3), a condition of continuing the anaerobic culture is that a pH value is 4-11, a time is 0.5 d-6 d, and a temperature is 5° C.-80° C.

Preferably, the nitrate is sodium nitrate or potassium nitrate.

More preferably, an addition amount of the nitrate does not exceed 50 mg/L.

Further preferably, with a volume of the mixture formed by mixing in step 2) as a reference, the concentration of the nitrate is 20 mg/L-24 mg/L.

Preferably, the bacteria include denitrifying bacteria and exoelectrogenic bacteria.

More preferably, the denitrifying bacteria include *Pseudomonas* and *Paracoccus denitrificans*, and the exoelectrogenic bacteria include *Shewanella* and *Geobacter*.

More preferably, a dry weight ratio of the denitrifying bacteria to the second urban organic waste is (0.001-20):100, and a dry weight ratio of the exoelectrogenic bacteria to the second urban organic waste is (0.001-20):100.

Further preferably, the dry weight ratio of the denitrifying bacteria to the second urban organic waste is (0.2-0.6):100, and the dry weight ratio of the exoelectrogenic bacteria to the second urban organic waste is (0.5-1.5):100.

Preferably, the organic acid includes acetic acid, propanoic acid or lactic acid; the hazardous substance includes heavy metal and antibiotic; the antibiotic includes tetracycline and sulfadiazine; and the heavy metal includes chromium and arsenic.

In the present invention, in a biological conversion process of an urban organic waste, microbes are introduced to eliminate hazardous substances such as antibiotics and heavy metals through degradation or oxidation reduction mechanism of microbes. With antibiotics as an electron donor and heavy metal ions as an electron acceptor, under the action of the microbes such as *Pseudomonas* and *Paracoccus denitrificans*, the antibiotic is degraded and completely mineralized while the heavy metal ions are reduced and detoxified. Since the exoelectrogenic bacteria have the capability to promote electron transfer or transport, the efficiency of the antibiotic degradation and heavy metal ion reduction will be significantly improved by adding the exoelectrogenic bacteria during an antibiotic degradation and heavy metal ion reduction process. Furthermore, metabolic products of acidogenic bacteria (for example, lactic acid) may be used as a carbon source required for growth and metabolism of the exoelectrogenic bacteria. As a result, the use of the present invention greatly promotes the elimination efficiency of the hazardous substances and increases a product yield of the organic acid for high-value anaerobic biological conversion of the urban organic waste.

Compared with prior art, the present invention has the following beneficial effects.

(1) In the present invention, the unfavorable effect of antibiotics and heavy metal ions in a process of biological conversion of the urban organic waste into an organic acid, for example, a high-value chemical, such as acetic acid, propanoic acid and lactic acid, is biologically reduced and the yield of the organic acid is increased by three folds.

(2) In the present invention, without using chemical agents, a residue amount of antibiotics and heavy metal ions after biological conversion of the urban organic waste is reduced, thereby improving the yield of products such as high quality organic acid, and significantly reducing secondary pollution to the environment resulting from the residues of the treatment of the urban organic waste.

BRIEF DESCRIPTIONS OF THE DRAWINGS

FIG. 1 is a flowchart illustrating a method of reducing and controlling a hazardous substance in a process of high-value biological conversion of an urban organic waste.

DETAILED DESCRIPTIONS OF EMBODIMENTS

The present invention will be further described below in combination with specific embodiments and those skilled in the art may know about other advantages and efficacies of the present invention easily from the contents disclosed in the specification.

Before the specific embodiments of the present invention are further described, it should be understood that the scope of protection of the present invention is not limited to the following specific embodiments. It should be further understood that the terms used in the embodiments are used for describing a particular solution rather than limiting the present invention. Those test methods without specific conditions specified in the following embodiments are generally carried out under normal conditions or under conditions recommended by each manufacturer.

When a value range is given in an embodiment, it should be understood that unless otherwise stated in the present invention, two endpoints of each value range and any value between the two endpoints may be selected. Unless otherwise defined, all technical or scientific terms used in the present invention has the same meaning as generally understood by those skilled in the art. In addition to the specific methods, devices and materials used in the embodiments, those skilled in the art may also use any method, device and material in the prior art which are similar or equivalent to the method, device and material mentioned in the embodiments of the present invention based on the knowledge of the prior art and the recordings of the present invention, so as to implement the present invention.

In one embodiment, the urban garbage includes restaurant garbage and/or kitchen garbage.

FIG. 1 shows a method of reducing and controlling a hazardous substance in a process of biological conversion of an urban organic waste. The method specifically includes the following steps.

1) Acclimation stage: a sludge, a first urban organic waste and an acid are mixed with water for acclimation to obtain an acclimatized sludge; specifically, a dry weight ratio of the sludge to the first urban organic waste is 1:(7-11), the acid is acetic acid, propanoic acid or lactic acid, a concentration of a solid in the mixture is 2000 mg/L-10000 mg/L, a concentration of the acid in the mixture is 50 mg/L-3000 mg/L, and the acclimation condition is that a pH value is 4-11 and a temperature is 5° C.-80° C.

2) Stage 1 of biological conversion: the acclimatized sludge is mixed with a second urban organic waste to perform anaerobic culture; specifically, a dry weight ratio of the acclimatized sludge to the second urban organic waste is (0.5-30):100, the mixture further includes water, a concentration of a solid in the mixture is 5000 mg/L-70000 mg/L, and a condition of the anaerobic culture is that a pH value is 4-11, a time is 0.5 d-6 d, and a temperature is 5° C.-80° C.

3) Stage 2 of biological conversion: nitrate and bacteria are added to continue anaerobic culture so as to obtain an organic acid; specifically, the nitrate is sodium nitrate or potassium nitrate; the bacteria include denitrifying bacteria and exoelectrogenic bacteria, and a condition of continuing anaerobic culture is that a pH value is 4-11, a time is 0.5 d-6 d, and a temperature is 5° C.-80° C.

As a preferred embodiment of the embodiments of the present invention, the denitrifying bacteria include *Pseudomonas* and *Paracoccus denitrificans*, and the exoelectrogenic bacteria include *Shewanella* and *Geobacter*.

As a preferred embodiment of the embodiments of the present invention, a dry weight ratio of the denitrifying bacteria to the second urban organic waste is (0.001-20): 100, and a dry weight ratio of the exoelectrogenic bacteria to the second urban organic waste is (0.001-20):100.

In the embodiments of the present invention, biological conversion is performed with the optimal dry weight ratio of the sludge to the first urban organic waste being 1:9.

Embodiment 1

The method of reducing and controlling a hazardous substance in a process of high-value biological conversion of an urban organic waste in the embodiment includes the following steps:

1) Acclimation stage: a residual sludge of a wastewater treatment plant, the first urban organic waste, acetic acid and water were placed in a biological acclimation reactor and mixed uniformly, where a dry weight ratio of the sludge to the first urban organic waste was 1:9, a concentration of a solid in the mixture was 10000 mg/L, a concentration of acetic acid in the mixture was 3000 mg/L; a pH value in the acclimation reactor was maintained as 11 and a temperature was maintained as 80° C., and a concentration of acetic acid in the acclimation reactor was measured each day; when the concentration of acetic acid in the reactor no longer increased noticeably over time, the above operations were performed again; through acclimation of 51 d, an acclimatized sludge (VS-A) was obtained.

2) Stage 1 of biological conversion: the second urban organic waste and the acclimatized sludge (VS-A) were added to a biological conversion reactor and mixed uniformly, where a dry weight ratio of VS-A to the second urban organic waste was 30:100; water was added until the concentration of a solid in the biological conversion reactor was 70000 mg/L; sulfadiazine, tetracycline, potassium dichromate and sodium arsenate were added to the biological conversion reactor in the amount of 10 mg/L respectively, and then stirred under an anaerobic condition for 6 days with the pH value controlled to 11 and a culture temperature to 80° C.

3) Stage 2 of biological conversion: potassium nitrate was added to a product of the biological conversion to 50 mg/L, where a dry weight ratio of *Pseudomonas* to the second urban organic waste was 0.001:100, and a dry weight ratio of *Shewanella* to the second urban organic waste was 0.001:100; the above mixture was stirred for 6 days and then solid-liquid separation was performed and then the concentrations of lactic acid, tetracycline, sulfadiazine, chromium ions and arsenic ions in the liquid phase were analyzed, and the concentrations of tetracycline, sulfadiazine, chromium ions and arsenic ions in the solid phase were analyzed.

As a result, the concentration of acetic acid in the liquid phase was 3241 mg/L, and the removal rates of total sulfadiazine, tetracycline, hexavalent chromium and pentavalent arsenic in the liquid and solid phases were 39%, 36%, 41% and 41%, respectively.

Embodiment 2, embodiment 3, embodiment 4 and control embodiment 1 are identical to the embodiment 1 except for specific parameters listed in table below. The specific parameters and detection results are shown in table below.

| Stage | Index | Embodiment 1 | Embodiment 2 | Embodiment 3 | Embodiment 4 | Control embodiment 1 |
|---|---|---|---|---|---|---|
| Acclimation stage | dry weight ratio of the sludge to the first urban organic waste | 1:9 | 1:9 | 1:9 | 1:9 | 1:9 |
| | concentration of acetic acid in the mixture/mg/L | 3000 | 3000 | 2100 | 2100 | 50 |
| | concentration of solid in the mixture/mg/L | 10000 | 10000 | 8000 | 8000 | 2000 |
| | acclimation pH | 11 | 11 | 9 | 9 | 4 |
| | acclimation temperature/° C. | 80 | 80 | 25 | 25 | 5 |
| | acclimation time/d | 51 | 51 | 46 | 46 | 60 |
| Stage 1 of biological conversion | dry weight ratio of the acclimatized sludge to the second urban organic waste | 30:100 | 30:100 | 8:100 | 8:100 | 0.5:100 |
| | solid concentration (mg/L) | 70000 | 70000 | 30000 | 30000 | 5000 |
| | culture pH | 11 | 11 | 9 | 9 | 4 |
| | culture temperature/° C. | 80 | 80 | 25 | 25 | 5 |
| | culture time/d | 6 | 6 | 1 | 3 | 1 |
| Stage 2 of biological conversion | nitrate and concentration/mg/L | potassium nitrate 50 | potassium nitrate 50 | sodium nitrate 22 | sodium nitrate 22 | — |
| | dry weight ratio of the bacteria to the second urban organic waste | Pseudomonas/0.001:100 Shewanella/0.001:100 | Pseudomonas/20:100 Geobacter 20:100 | paracoccus denitrificans/0.4:100 Geobacter/1:100 | paracoccus denitrificans/0.4:100 Shewanella/1:100 | |
| | continued conversion time/d | 6 | 6 | 1 | 3 | |
| Product | acetic acid/mg/L | 3241 | 2138 | 3038 | 4967 | 1096 |
| | sulfadiazine removal rate/% | 39 | 43 | 61 | 83 | 12 |
| | tetracycline removal rate/% | 36 | 42 | 63 | 81 | 10 |
| | Chromium removal rate/% | 41 | 50 | 68 | 89 | 22 |
| | arsenic removal rate/% | 41 | 47 | 61 | 88 | 19 |

Embodiment 5

The method of reducing and controlling a hazardous substance in a process of high-value biological conversion of an urban organic waste in the embodiment includes the following steps.

1) Acclimation stage: a residual sludge of a wastewater treatment plant, the first urban organic waste, propanoic acid and water were placed in a biological acclimation reactor and mixed uniformly, where a dry weight ratio of the sludge to the first urban organic waste was 1:9, a concentration of a solid in the mixture was 10000 mg/L, a concentration of propanoic acid in the mixture was 3000 mg/L; a pH value in the acclimation reactor was maintained as 11 and a temperature was maintained as 80° C., and a concentration of propanoic acid in the acclimation reactor was measured each day; when the concentration of propanoic acid in the reactor no longer increased noticeably over time, the above operations were performed again; through acclimation of 49 d, an acclimatized sludge (VS-P) was obtained.

2) Stage 1 of biological conversion: the second urban organic waste and the acclimatized sludge (VS-P) were added to a biological conversion reactor and mixed uniformly, where a dry weight ratio of VS-P to the second urban organic waste was 30:100; water was added until the concentration of a solid in the biological conversion reactor was 70000 mg/L; sulfadiazine, tetracycline, potassium dichromate and sodium arsenate were added to the biological conversion reactor in the amount of 10 mg/L respectively, and then stirred under an anaerobic condition for 6 days with the pH value controlled to 11 and a culture temperature to 80° C.

3) Stage 2 of biological conversion: potassium nitrate was added to a product of the biological conversion to 50 mg/L, and Pseudomonas and Shewanella were then added, where a dry weight ratio of Pseudomonas to the second urban organic waste was 0.001:100, and a dry weight ratio of Shewanella to the second urban organic waste was 0.001:100; the above mixture was stirred for 6 days and then solid-liquid separation was performed and then the concentrations of lactic acid, tetracycline, sulfadiazine, chromium ions and arsenic ions in the liquid phase were analyzed, and the concentrations of tetracycline, sulfadiazine, chromium ions and arsenic ions in the solid phase were analyzed.

As a result, the concentration of propanoic acid in the liquid phase was 1394 mg/L, and the removal rates of total sulfadiazine, tetracycline, hexavalent chromium and pentavalent arsenic in the liquid and solid phases were 31%, 33%, 44% and 45% respectively.

Embodiment 6, embodiment 7, embodiment 8 and control embodiment 2 are identical to the embodiment 5 except for specific parameters listed in table below. The specific parameters and detection results are shown in table below.

| Stage | Index | Embodiment 5 | Embodiment 6 | Embodiment 7 | Embodiment 8 | Control embodiment 2 |
|---|---|---|---|---|---|---|
| Acclimation stage | dry weight ratio of the sludge to the first urban organic waste | 1:9 | 1:9 | 1:9 | 1:9 | 1:9 |
| | concentration of acetic acid in the mixture/mg/L | 3000 | 3000 | 1200 | 1200 | 50 |
| | concentration of solid in the mixture/mg/L | 10000 | 10000 | 8000 | 8000 | 2000 |
| | acclimation pH | 11 | 11 | 8 | 8 | 4 |
| | acclimation temperature/° C. | 80 | 80 | 25 | 25 | 5 |
| | acclimation time/d | 49 | 56 | 44 | 42 | 58 |
| Stage 1 of biological conversion | dry weight ratio of the acclimatized sludge to the second urban organic waste | 30:100 | 30:100 | 8:100 | 8:100 | 0.5:100 |
| | solid concentration/mg/L | 70000 | 70000 | 30000 | 30000 | 5000 |
| | culture pH | 11 | 11 | 8 | 9 | 4 |
| | culture temperature/° C. | 80 | 80 | 25 | 25 | 5 |
| | culture time/d | 6 | 6 | 1 | 2.5 | 1 |
| Stage 2 of biological conversion | nitrate and concentration/mg/L | potassium nitrate 50 | potassium nitrate 50 | sodium nitrate 22 | sodium nitrate 22 | — |
| | dry weight ratio of the bacteria to the second urban organic waste | Pseudomonas/ 0.001:100 Shewanella/ 0.001:100 | Pseudomonas/ 20:100 Geobacter/ 20:100 | paracoccus denitrificans/ 0.4:100 Geobacter/ 1:100 | paracoccus denitrificans/ 0.4:100 Shewanella/ 1:100 | |
| | continued conversion time/d | 6 | 6 | 1 | 2.5 | |
| Product | propanoic acid/mg/L | 1394 | 906 | 2367 | 3385 | 604 |
| | sulfadiazine removal rate/% | 31 | 28 | 68 | 86 | 12 |
| | tetracycline removal rate/% | 33 | 24 | 65 | 83 | 13 |
| | chromium removal rate/% | 44 | 40 | 71 | 90 | 21 |
| | arsenic removal rate/% | 45 | 43 | 73 | 93 | 22 |

Embodiment 9

The method of reducing and controlling a hazardous substance in a process of high-value biological conversion of an urban organic waste in the embodiment includes the following steps:

1) Acclimation stage: a residual sludge of a wastewater treatment plant, the first urban organic waste, lactic acid and water were placed in a biological acclimation reactor and mixed uniformly, where a dry weight ratio of the sludge to the first urban organic waste was 1:9, a concentration of a solid in the mixture was 10000 mg/L, a concentration of lactic acid in the mixture was 3000 mg/L; a pH value in the acclimation reactor was maintained as 11 and a temperature was maintained as 80° C., and a concentration of lactic acid in the acclimation reactor was measured each day; when the concentration of lactic acid in the reactor no longer increased noticeably over time, the above operations were performed again; through acclimation of 46 d, an acclimatized sludge (VS-L) was obtained.

2) Stage 1 of biological conversion: the second urban organic waste and the acclimatized sludge (VS-L) were added to a biological conversion reactor and mixed uniformly, where a dry weight ratio of VS-L to the second urban organic waste was 30:100; water was added until the concentration of a solid in the biological conversion reactor was 70000 mg/L; sulfadiazine, tetracycline, potassium dichromate and sodium arsenate were added to the biological conversion reactor in the amount of 10 mg/L respectively, and then stirred under an anaerobic condition for 6 days with the pH value controlled to 11 and a culture temperature to 80° C.

3) Stage 2 of biological conversion: potassium nitrate was added to a product of the biological conversion to 50 mg/L, and *Pseudomonas* and *Shewanella* were then added, where a dry weight ratio of *Pseudomonas* to the second urban organic waste was 0.001:100, and a dry weight ratio of *Shewanella* to the second urban organic waste was 0.001:100; the above mixture was stirred for 6 days and then solid-liquid separation was performed and then the concentrations of lactic acid, tetracycline, sulfadiazine, chromium ions and arsenic ions in the liquid phase were analyzed, and the concentrations of tetracycline, sulfadiazine, chromium ions and arsenic ions in the solid phase were analyzed.

As a result, the concentration of lactic acid in the liquid phase was 1071 mg/L, and the removal rates of total sulfadiazine, tetracycline, hexavalent chromium and pentavalent arsenic in the liquid and solid phases were 43%, 36%, 48% and 50% respectively.

Embodiment 10, embodiment 11, embodiment 12, and control embodiment 3 are identical to the embodiment 9 except for specific parameters listed in table below. The specific parameters and detection results are shown in table below.

| Stage | Index | Embodiment 9 | Embodiment 10 | Embodiment 11 | Embodiment 12 | Control embodiment 3 |
|---|---|---|---|---|---|---|
| Acclimation stage | dry weight ratio of the sludge to the first urban organic waste | 1:9 | 1:9 | 1:9 | 1:9 | 1:9 |
| | concentration of acetic acid in the mixture/mg/L | 3000 | 3000 | 600 | 600 | 50 |
| | concentration of solid in the mixture/mg/L | 10000 | 10000 | 8000 | 8000 | 2000 |
| | Acclimation pH | 11 | 11 | 6.5 | 8 | 4 |
| | acclimation temperature/° C. | 80 | 80 | 25 | 25 | 5 |
| | acclimation time/d | 46 | 43 | 38 | 35 | 42 |
| Stage 1 of biological conversion | dry weight ratio of the acclimatized sludge to the second urban organic waste | 30:100 | 30:100 | 8:100 | 8:100 | 0.5:100 |
| | solid concentration/mg/L | 70000 | 70000 | 30000 | 30000 | 5000 |
| | culture pH | 11 | 11 | 6.5 | 6.5 | 4 |
| | culture temperature/° C. | 80 | 80 | 25 | 25 | 5 |
| | culture time/d | 6 | 6 | 1 | 2 | 1 |
| Stage 2 of biological conversion | nitrate and concentration/mg/L | potassium nitrate 50 | potassium nitrate 50 | sodium nitrate 22 | sodium nitrate 22 | — |
| | dry weight ratio of the bacteria to the second urban organic waste | *Pseudomonas*/ 0.001:100 *Shewanella*/ 0.001:100 | *Pseudomonas*/ 20:100 *Geobacter*/ 20:100 | *paracoccus denitrificans*/ 0.4:100 *Geobacter*/ 1:100 | *paracoccus denitrificans*/ 0.4:100 *Shewanella*/ 1:100 | |
| | continued conversion time/d | 6 | 6 | 1 | 2 | |
| Product | propanoic acid/mg/L | 1071 | 936 | 1482 | 2407 | 548 |
| | sulfadiazine removal rate/% | 43 | 41 | 73 | 90 | 22 |
| | tetracycline removal rate/% | 36 | 35 | 74 | 86 | 18 |
| | chromium removal rate/% | 48 | 45 | 78 | 92 | 28 |
| | arsenic removal rate/% | 50 | 41 | 80 | 89 | 34 |

Embodiment 13

The method of reducing and controlling a hazardous substance in a process of high-value biological conversion of an urban organic waste in the embodiment includes the following steps.

1) Acclimation stage: a residual sludge of a wastewater treatment plant, the first urban organic waste, lactic acid and water were placed in a biological acclimation reactor and mixed uniformly, where a dry weight ratio of the sludge to the first urban organic waste was 1:7, a concentration of a solid in the mixture was 10000 mg/L, a concentration of lactic acid in the mixture was 3000 mg/L; a pH value in the acclimation reactor was maintained as 11 and a temperature was maintained as 80° C., and a concentration of lactic acid in the acclimation reactor was measured each day; when the concentration of lactic acid in the reactor no longer increased noticeably over time, the above operations were performed again; through acclimation of 46 d, an acclimatized sludge (VS-L) was obtained.

2) Stage 1 of biological conversion: the second urban organic waste and the acclimatized sludge (VS-L) were added to a biological conversion reactor and mixed uniformly, where a dry weight ratio of VS-L to the second urban organic waste was 30:100; water was added until the concentration of a solid in the biological conversion reactor was 70000 mg/L; sulfadiazine, tetracycline, potassium dichromate and sodium arsenate were added to the biological conversion reactor in the amount of 10 mg/L respectively, and then stirred under an anaerobic condition for 6 days with the pH value controlled to 11 and a culture temperature to 80° C.

3) Stage 2 of biological conversion: potassium nitrate was added to a product of the biological conversion to 50 mg/L, and *Pseudomonas* and *Shewanella* were then added, where a dry weight ratio of *Pseudomonas* to the second urban organic waste was 0.001:100, and a dry weight ratio of *Shewanella* to the second urban organic waste was 0.001:100; the above mixture was stirred for 6 days and then solid-liquid separation was performed and then the concentrations of lactic acid, tetracycline, sulfadiazine, chromium ions and arsenic ions in the liquid phase were analyzed, and the concentrations of tetracycline, sulfadiazine, chromium ions and arsenic ions in the solid phase were analyzed.

As a result, the concentration of lactic acid in the liquid phase was 948 mg/L, and the removal rates of total sulfadiazine, tetracycline, hexavalent chromium and pentavalent arsenic in the liquid and solid phases were 36%, 30%, 37% and 41% respectively.

Embodiment 14

The method of reducing and controlling a hazardous substance in a process of high-value biological conversion of an urban organic waste in the embodiment includes the following steps.

1) Acclimation stage: a residual sludge of a wastewater treatment plant, the first urban organic waste, lactic acid and water were placed in a biological acclimation reactor and mixed uniformly, where a dry weight ratio of the sludge to the first urban organic waste was 1:11, a concentration of a solid in the mixture was 10000 mg/L, a concentration of lactic acid in the mixture was 3000 mg/L; a pH value in the acclimation reactor was maintained as 11 and a temperature was maintained as 80° C., and a concentration of lactic acid in the acclimation reactor was measured each day; when the concentration of lactic acid in the reactor no longer increased noticeably over time, the above operations were performed again; through acclimation of 46d, an acclimatized sludge (VS-L) was obtained.

2) Stage 1 of biological conversion: the second urban organic waste and the acclimatized sludge (VS-L) were added to a biological conversion reactor and mixed uniformly, where a dry weight ratio of VS-L to the second urban organic waste was 30:100; water was added until the concentration of a solid in the biological conversion reactor was 70000 mg/L; sulfadiazine, tetracycline, potassium dichromate and sodium arsenate were added to the biological conversion reactor in the amount of 10 mg/L respectively, and then stirred under an anaerobic condition for 6 days with the pH value controlled to 11 and a culture temperature to 80° C.

3) Stage 2 of biological conversion: potassium nitrate was added to a product of the biological conversion to 50 mg/L, and *Pseudomonas* and *Shewanella* were then added, where a dry weight ratio of *Pseudomonas* to the second urban organic waste was 0.001:100, and a dry weight ratio of *Shewanella* to the second urban organic waste was 0.001:100; the above mixture was stirred for 6 days and then solid-liquid separation was performed and then the concentrations of lactic acid, tetracycline, sulfadiazine, chromium ions and arsenic ions in the liquid phase were analyzed, and the concentrations of tetracycline, sulfadiazine, chromium ions and arsenic ions in the solid phase were analyzed.

As a result, the concentration of lactic acid in the liquid phase was 981 mg/L, and the removal rates of total sulfadiazine, tetracycline, hexavalent chromium and pentavalent arsenic in the liquid and solid phases were 40%, 32%, 43% and 46% respectively.

The above embodiments are merely intended to illustrate the principle and efficacies of the present invention rather than limit the present invention. Any modification or change may be made to the above embodiments by those skilled in the art without departing from the spirit and scope of the present invention. Therefore, all equivalent modifications or changes completed by persons of ordinary skill in the prior art without departing from the spirit and technical idea of the present invention shall all be covered by the claims of the present invention.

What is claimed is:

1. A method of reducing and controlling a hazardous substance in a process of biological conversion of an urban organic waste, comprising the following steps:
   1) Acclimation stage: mixing a sludge, a first urban organic waste and a first organic acid solution with water in a mixture for acclimation to obtain an acclimatized sludge;
   2) Stage 1 of biological conversion: mixing the acclimatized sludge with a second urban organic waste to perform anaerobic culture;
   3) Stage 2 of biological conversion: adding nitrate and bacteria to continue anaerobic culture so as to obtain a second organic acid solution and a residue;
   wherein the mixture has a first amount of the hazardous substance; the second urban organic waste has a second amount of the hazardous substance; the residue has a third amount of the hazardous substance; and wherein the third amount is lower than a total of the first amount and the second amount; and
   wherein the hazardous substance comprises at least one of heavy metals and antibiotics.

2. The method of claim 1, wherein in step 1), a dry weight ratio of the sludge to the first urban organic waste is 1:(7-11);

and/or, the acclimation condition is that a pH value is 4-11, and a temperature is 5° C.-80° C.;

and/or, the first organic acid solution comprises at least one of acetic acid, propanoic acid and lactic acid;

and/or, a content of a solid in the mixture formed by mixing is 2000 mg/L-10000 mg/L;

and/or, a concentration of the acid in the mixture formed by mixing is 50 mg/L-3000 mg/L.

3. The method of claim 1, wherein in step 2), a dry weight ratio of the acclimatized sludge to the second urban organic waste is (0.5-30):100;

and/or, the mixture formed by mixing further comprises water, and a concentration of a solid in the mixture is 5000 mg/L-70000 mg/L.

4. The method of claim 1, wherein in steps 2) and 3), a time of the anaerobic culture is 0.5d-6d with a pH value of 4-11 and a temperature of 5° C.-80° C.

5. The method of claim 1, wherein the nitrate is sodium nitrate or potassium nitrate; the bacteria comprise denitrifying bacteria and exoelectrogenic bacteria.

6. The method of claim 5, wherein the denitrifying bacteria comprise *pseudomonas* and *paracoccus denitrificans*, and the exoelectrogenic bacteria comprise *shewanella* and *geobacter*.

7. The method of claim 5, wherein an addition amount of the nitrate does not exceed 50 mg/L.

8. The method of claim 5, wherein a dry weight ratio of the denitrifying bacteria to the second urban organic waste is (0.001-20):100, and a dry weight ratio of the exoelectrogenic bacteria to the second urban organic waste is (0.001-20): 100.

9. The method of claim 1, wherein the sludge is a residual sludge of a wastewater treatment plant; and the urban organic waste comprises restaurant garbage and kitchen garbage.

10. The method of claim 1, wherein each of the first organic acid solution and the second organic solution comprises at least one of acetic acid, propanoic acid and lactic acid; the antibiotics comprise tetracycline and sulfanilamide; and the heavy metals comprise chromium and arsenic.

* * * * *